United States Patent [19]

Price

[11] 3,998,213

[45] Dec. 21, 1976

[54] SELF-ADJUSTABLE HOLDER FOR AUTOMATICALLY POSITIONING ELECTROENCEPHALOGRAPHIC ELECTRODES

[75] Inventor: Robert A. Price, New York, N.Y.

[73] Assignee: Bio-Volt Corporation, New York, N.Y.

[22] Filed: Apr. 8, 1975

[21] Appl. No.: 566,139

[52] U.S. Cl. .................. 128/2.1 B; 128/2.1 E; 128/DIG. 4; 128/410
[51] Int. Cl.² ............................. A61B 5/04
[58] Field of Search ......... 128/2.1 E, 2.1 B, 2.06 E, 128/DIG. 4, 404, 410, 416–418

[56] References Cited
UNITED STATES PATENTS

| | | | |
|---|---|---|---|
| 2,409,033 | 10/1946 | Garceau | 128/2.1 B |
| 2,426,958 | 9/1947 | Ulett | 128/2.1 B |
| 2,549,836 | 4/1951 | McIntyre et al. | 128/2.1 B |
| 2,872,926 | 2/1959 | Aldermen | 128/410 |
| 2,943,627 | 7/1960 | Howell | 128/416 |
| 3,387,608 | 6/1968 | Figar | 128/2.06 E |
| 3,411,495 | 11/1968 | Casby | 128/2.1 B |
| 3,490,439 | 1/1970 | Rolston | 128/2.1 E |
| 3,508,541 | 4/1970 | Westbrook et al. | 128/2.1 E |
| 3,623,477 | 11/1971 | Trent | 128/2.1 B |
| 3,658,054 | 4/1972 | Iberall | 128/2.1 B |
| 3,735,753 | 5/1973 | Pisarski | 128/2.1 E |

FOREIGN PATENTS OR APPLICATIONS 166,446   1/1963   U.S.S.R. ................. 128/2.1 E

OTHER PUBLICATIONS

Henley et al, "Electrode Systems For Recording the EEG In Active Subjects", Biomed. Electrode Technology, Academic Press, 1974.
Jasper, "10–20 Electrode System...Federation", EEG Clinical Neurophysiology, vol. 10, pp. 371–375, 1958.

*Primary Examiner*—Robert W. Michell
*Assistant Examiner*—Lee S. Cohen
*Attorney, Agent, or Firm*—Brumbaugh, Graves, Donohue & Raymond

[57] ABSTRACT

A self-adjustable holder for automatically positioning electroencephalographic electrodes on the head of an animal in accordance with the International 10/20 System. This holder comprises a cap which is expandable and elastic so as to self-adjust to a snug fit when in place on the head, and a plurality of electrode positioning elements located on and attached to the cap at various points thereon. Each electrode positioning element is designed to hold an associated electrode in contact with the head at a precise position, with respect to at least one reference point on the head, in accordance with the International 10/20 System.

20 Claims, 12 Drawing Figures

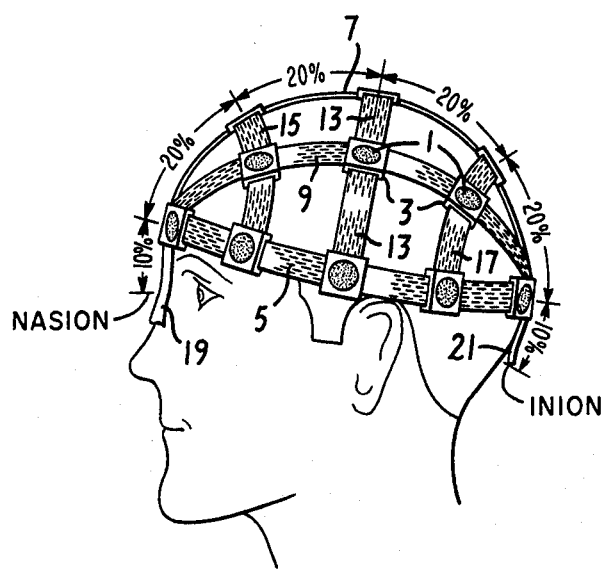
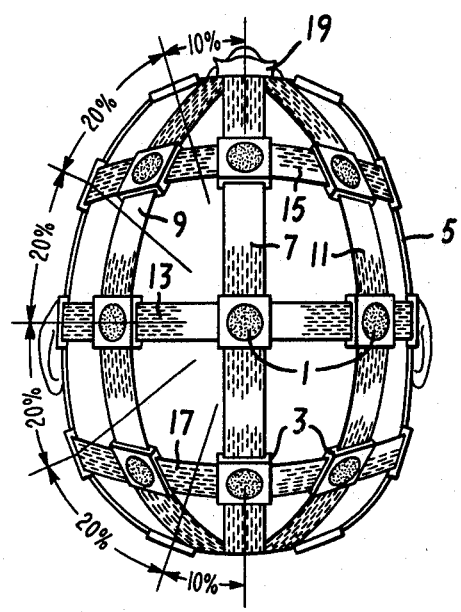
FIG. 1
FIG. 2
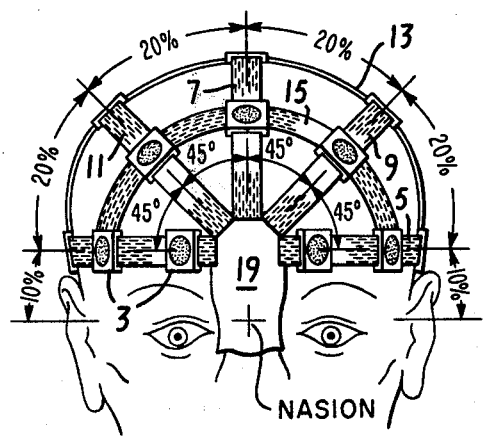
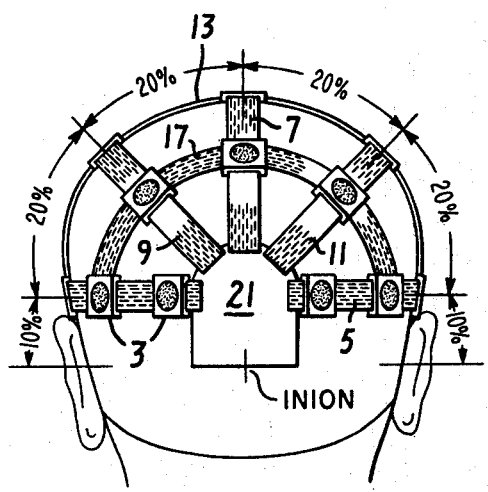
FIG. 3
FIG. 4

U.S. Patent  Dec. 21, 1976  Sheet 2 of 3  3,998,213
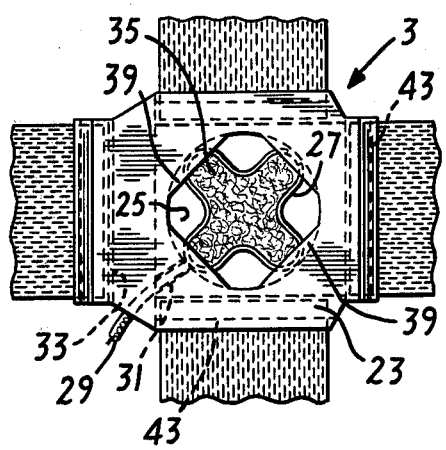
FIG. 5
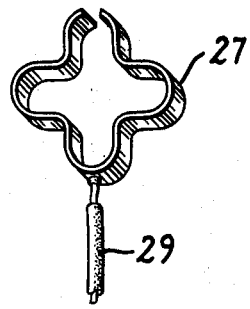
FIG. 8
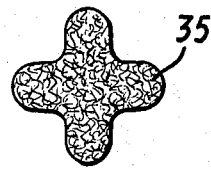
FIG. 9
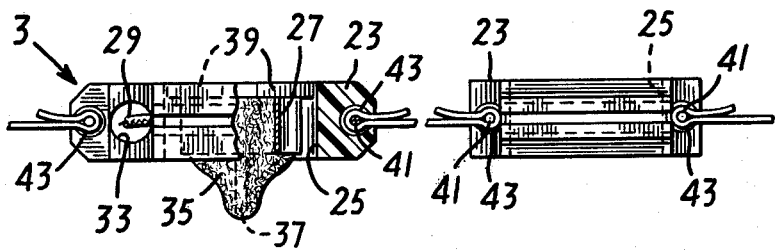
FIG. 6  FIG. 7
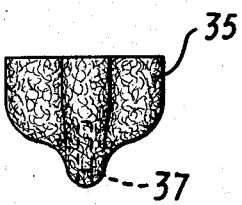
FIG. 10
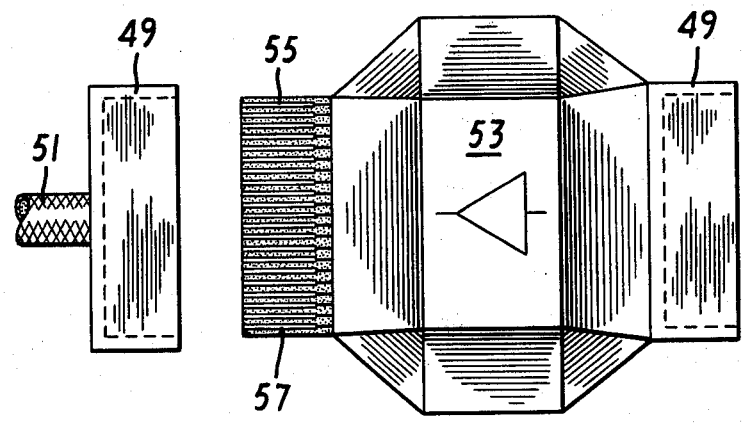
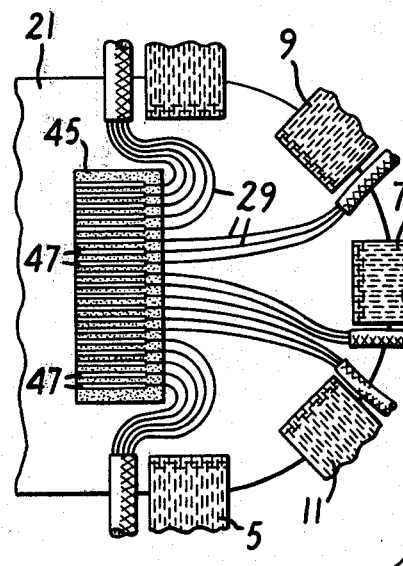
FIG. 12

SELF-ADJUSTABLE HOLDER FOR AUTOMATICALLY POSITIONING ELECTROENCEPHALOGRAPHIC ELECTRODES

BACKGROUND OF THE INVENTION

The present invention relates to an electrode holder; that is, more particularly, to a self-adjustable electrode holder for automatically positioning electroencephalographic electrodes.

An electroencephalograph is an instrument for recording the electrical activity of an animal brain which is sensed by means of electrodes positioned at the surface of the scalp. The instrument is used in the study of the normal brain as well as in the diagnosis of epilepsy, trauma, tumors and other degenerations of the brain.

An electroencephalograph conventionally comprises a plurality of electrodes, a holding means for maintaining the electrodes in contact with the scalp, an electronic circuit including amplifiers and controls for processing electrical signals received at the electrodes, and an output device, such as an oscillograph, for converting the data into readable form. The electrodes, the electronic circuit and the output device are, of course, interconnected by means of wires or cables.

Neither the electronic circuit nor the output device form a part of the present invention so that no description of their construction or method of operation need be given in this specification.

An electroencephalographic technician normally administers or obtains an electroencephalograph from a patient in the following manner: While the patient is seated, the technician carefully measures the patient's head and determines the points at which the electrodes are to be placed. Electrodes are then secured to the patient's head at these points by means of a conductive paste, in the nature of an adhesive, which hardens (but which can be subsequently washed away with soap and water). Thereafter, the technician operates the controls of the electronic circuit and determines whether each of the electrodes is in proper electrical contact with the scalp. If so, the signals received at the electrodes are recorded for subsequent reading by a neurologist.

The electroencephalographic technique described above requires both knowledge and skill to properly locate and attach the electrodes to the patient's head. Moreover, this process is time-consuming. It normally takes an excess of 45 minutes to completely "wire" a patient in preparation for an electroencephalographic recording.

Various attempts have been made to provide a "helmet" or other holder device which would enable a technician, without extensive training, to properly position and hold the electroencephalographic electrodes in contact with a patient's head within a short period of time, say five to 10 minutes. These prior art attempts have been mildly successful but have not achieved wide use in the field because the electrode positions for each different head still have to be measured and the holder or helmet adjusted to apply the electrodes at these positions. In addition, it is necessary, in some cases, to adjust the helmet itself to the specific size of a patient's head. Furthermore, depending upon the type of electrode used, it has been difficult to make proper contact between the electrode and the scalp.

It should be noted that the positions of electrodes on the head of a patient have been standardized since about 1959 so that electroencephalographs obtained from various patients may be compared. This standard, which is called the International 10/20 System, is well known and is described by H. H. Jasper in EEG Clinical Neurophysiology, Vol. 10, page 371 (1958).

SUMMARY OF THE INVENTION

It is therefore an object of the present invention to provide a holder for maintaining electroencephalographic electrodes in position on a patient's head.

It is a specific object of the present invention to provide a holder of the above-described type which will self-adjust to fit snugly on a patient's head.

It is a further specific object of the present invention to provide a holder of the above-described type which will automatically position the electroencephalographic electrodes on a patient's head in accordance with the International 10/20 System.

These objects, as well as other objects which will become apparent in the discussion that follows, are achieved, according to the present invention, by constructing the electroencephlographic electrode holder of (1) a cap which is expandable and elastic so as to self-adjust to a snug fit when in place on a patient's head and (2) a plurality of electrode positioning elements attached to the cap, each of which is designed to hold an associated electrode in a precise position in contact with the head when the cap is in place. The electrode positioning elements are located on the cap so as to position the electrodes in accordance with the International 10/20 System.

Because the cap is expandable and elastic, the electroencephalographic electrode holder according to the present invention is self-adjustable to fit different heads of various shapes and sizes. As the cap contracts or expands to snugly fit a particular head, the electrode positioning elements move closer together or farther apart from each other in equal proportions so that the spacing between the electrodes, once established in accordance with the International 10/20 System for a head of a given size, remains as prescribed by the 10/20 System for a head of another size.

In a preferred embodiment of the present invention the cap is made of a stretchable material such as rubber or a synthetic fiber mesh (e.g., nylon). When intended for use on an infant's or other person's head having little or no hair, the cap may be made substantially hemispherical in shape, similar to a bathing cap or hair net, so as to completely cover the top of the patient's head. When hair is present, it is preferable to construct the cap of a plurality of elongate members, such as straps, so that the hair may be parted by the technician to expose the scalp at each point at which the scalp is to be contacted by an electroencephalographic electrode.

If the cap is constructed of a plurality of elongate members, these members must be arranged and connected in a particular pattern, according to a preferred embodiment of the present invention, so as to locate the electrode positioning elements in accordance with the International 10/20 System. A number of such patterns of construction of a cap formed of elongate members will be described in detail hereinbelow.

Pursuant to a preferred feature of the electroencephalographic electrode holder according to the present invention, the cap is provided with means for precisely orienting and locating the cap with reference to the nasion and/or inion of the head when the cap is placed thereon. This locating means preferably includes a rigid member on opposite sides of the cap adapted to be positioned at the nasion and/or inion when the cap is in place.

Pursuant to another preferred feature of the present invention, the electrode positioning elements are made of rigid material and have an opening therethrough for the insertion of an associated electrode. Each element is provided with means, such as a flange portion, for retaining the electrode and means, such as a silver sleeve on the inside surface of the opening, for electrically contacting the electrode, when the electrode is inserted in the opening. Preferably, the sleeve is made substantially "star-shaped" so as to receive a star-shaped electrode. Such an arrangement prevents rotation of the electrode and provides for maximum electrical contact therewith in an area close to the point of contact with the scalp, so as to reduce, as much as possible, the level of noise and minimize resistance. The electrode preferably comprises an electrically conductive sponge which is saturated with a conductive cream or jell.

According to a further preferred feature of the present invention, the electroencephalographic electrode holder includes a socket or plug attached to the cap which serves as a detachable electrical connector for a plurality of wires connected to the various electrode positioning elements. In this way, the holder may be cleaned, stored and handled separately by the technician and connected into the electroencephalographic instrument only when in actual use.

In order to provide the maximum signal-to-noise ratio, the signal from each electrode may be amplified by a small preamplifier at a point physically close to the electrode itself. For example, each electrode positioning element may be provided with its own preamplifier as an integral part thereof, or all preamplifiers may be arranged together on a single plug-in unit. This plug-in unit is preferably adapted to mate with the electrical connector attached to the cap.

BRIEF DESCRIPTION OF THE DRAWINGS

FIG. 1 is a side view of a human head on which is placed an electroencephalographic electrode holder in accordance with a preferred embodiment of the present invention.

FIG. 2 is a top view of the head and holder illustrated in FIG. 1.

FIG. 3 is a front view of the head and holder illustrated in FIG. 1.

FIG. 4 is a rear view of the head and holder illustrated in FIG. 1.

FIG. 5 is a plan view of an electrode positioning element according to a preferred embodiment of the present invention.

FIG. 6 is a side view of the electrode positioning element of FIG. 5.

FIG. 7 is another side view of the electrode positioning element of FIG. 5.

FIG. 8 is a perspective view of a sleeve, for use in the electrode positioning element of FIG. 5, for contacting an associated electrode.

FIG. 9 is a top view of a disposable electrode for use with the electrode positioning element of FIG. 5.

FIG. 10 is a side view of the disposable electrode of FIG. 9.

FIG. 12 is a diagram showing an electrical connector arranged on the electroencephalographic electrode holder, and a preamplifier unit adapted to be plugged into the electrical connector in accordance with a preferred embodiment of the present invention.

DESCRIPTION OF THE PREFERRED EMBODIMENTS

Figure 11:
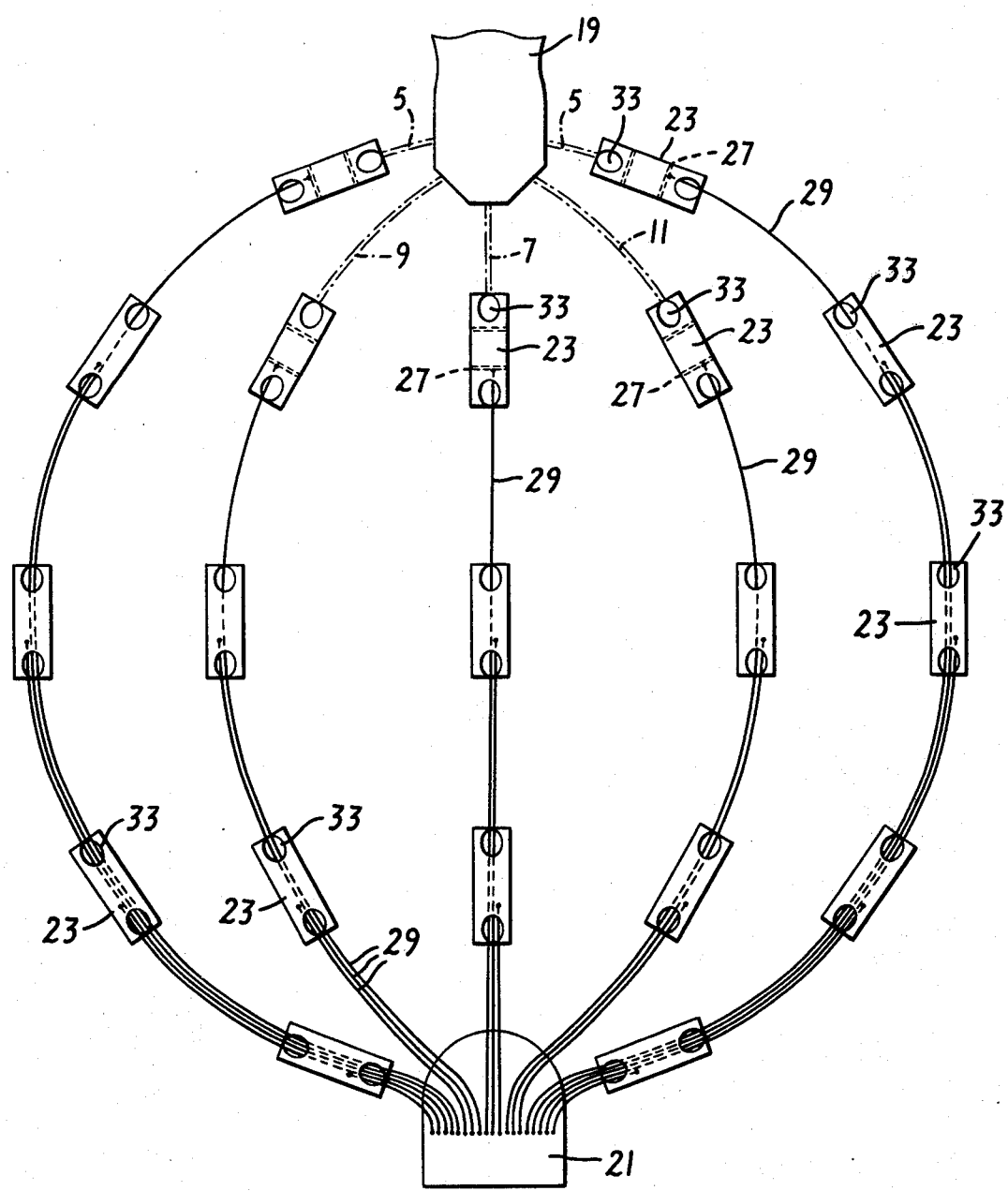
FIG. 11 is a wiring diagram illustrating the electrical connections to a plurality of electrode positioning elements according to a preferred embodiment of the present invention.

The preferred embodiments of the present invention will now be described with reference to FIGS. 1–12. As is customary, identical elements in the various figures have been designated with the same reference numerals.

FIGS. 1–4 illustrate the basic construction of the self-adjustable holder, according to the present invention, for automatically positioning electroencephalographic electrodes in accordance with the International 10/20 System. In these figures, the holder is shown in place on the head of an adult, male human being. As will be appreciated from the following description, however, the holder is adapted to fit the head of any human being, infant or adult, male or female, and, indeed, the head of any animal from which an electroencephalograph may be taken. The term "animal" is used in this specification in its broad, generic sense to include any living being (as distinguished from plants).

As pointed out above, the electrode holder according to the present invention comprises an expandable, elastic cap to which are attached a plurality of electrode positioning elements. In one preferred embodiment, the cap is substantially hemispherical in shape, much in the nature of a bathing cap, and is stretchable to fit snugly over heads of various sizes. A cap of this type may be made of rubber or a stretchable plastic material, or it may be made of a synthetic fiber mesh such as nylon cloth or the like.

In an alternative preferred embodiment, which is shown in FIGS. 1–4, the cap is made of a plurality of elongate members which are connected together in a particular pattern or configuration. As in the hemispherical embodiment referred to above, the elongate members may be made of rubber or stretchable plastic, or they may comprise an elastic cloth of any conventional type, such as the material used in the manufacture of stretchable belts or the like. The elongate members may be formed as single strips of material, or they may be hollow to permit the insertion of air or some other fluid to control their size.

In the embodiment shown in FIGS. 1–4, the elongate members of the holder are shown as simple elastic straps. These straps are arranged in a particular configuration which is adapted to the International 10/20 System for positioning electroencephalographic electrodes. In the illustrated embodiment, the electrodes 1 are located and held in position by the electrode positioning elements 3.

There are actually two strap configurations shown in superimposed form in FIGS. 1–4. The first configuration comprises:

1. A first strap 5 of generally circular shape adapted to surround the head in a substantially horizontal plane at the so-called "Central Line" of the International 10/20 System;

2. A second strap 7 of generally semi-circular shape attached to the first strap at the front and rearmost points thereof and adapted to extend over the top of the head in a substantially vertical plane;

3. A third strap 9 of generally semi-circular shape attached to the first strap at the front and rearmost points thereof and adapted to extend over the head in a plane forming an angle of 45° with respect to the vertical plane of the second strap;

4. A fourth strap 11 of generally semi-circular shape attached to the first strap at the front and rearmost points thereof and adapted to extend over the head in a plane forming an angle of 45° with respect to the vertical plane of the second strap.

A second strap configuration, which may be used in lieu of, or in addition to, the first configuration comprises:

1. The same first strap 5 adapted to surround the head at the Central Line;

2. A second strap 13 of generally semi-circular shape attached to the first strap 5 at points adjacent the ears and adapted to extend over the top of the head from side to side in a substantially vertical plane;

3. A third strap 15 of generally semi-circular shape attached to the first strap 5 so as to extend from side to side over the front portion of the head;

4. A fourth strap 17 of generally semi-circular shape attached to the first strap 5 so as to extend from side to side over the rear portion of the head.

As may be most easily seen in FIGS. 1 and 2, the third and fourth straps 15 and 17, respectively, of the second configuration extend generally in a plane which makes a slight angle with the plane of the second strap 13.

In accordance with the International 10/20 System, the electrode positions, which are indicated by the electrodes 1 in the positioning elements 3, are arranged at points which are staggered by distances that are either ten or twenty percent of the nasion-inion distance (FIGS. 1 and 2) or the length of a line extending over the top of the head from a substantially horizontal plane passing through the nasion and inion (FIGS. 3 and 4). These ten and twenty percent relationships, which are specified by the International 10/20 System (hence the term 10/20), are substantially maintained with the self-adjustable holder according to the present invention notwithstanding differences in the size and shape of the heads of different patients. Since the straps of the holder are expandable and elastic, they will expand or contract to fit snugly onto each head and will, consequently, cause each electrode positioning element to be automatically placed at the proper distance with respect to its adjacent positioning elements.

It will be appreciated from the discussion above that the electroencephalographic holder according to the present invention may be constructed of elongate members (e.g., straps) in either one of the two configurations described above. In the alternative, it may be constructed as the superposition of both configurations as is illustrated in FIGS. 1-4. The latter arrangement, in which the straps are "criss-crossed" over the head is slightly more expensive to manufacture but provides a slight improvement in the accuracy of location of the electrodes.

In order that the electroencephalographic technician may properly locate and orient the electroencephalographic holder on the head of a patient, two members 19 and 21 are provided to fix the position of the holder with reference to the nasion and the inion of the head, respectively. The member 19 is designed to fit onto the bridge of the nose of the patient, whereas the member 21 is merely positioned by the technician in relation to the inion. If desired, the members 19 and 21 may be made adjustable along their vertical axes so as to accurately locate the Central Line above the nasion and inion at exactly ten percent of the length of a line extending over the top of the head from a substantially horizontal plane passing through the nasion and the inion. However, when the holder is intended for use with normal adult human patients, the variation between patients in this ten percent distance may be ignored.

While the two members 19 and 21 may be made of the same elastic material as the elongate members of the cap, the two members are preferably made of a rigid material such as plastic.

FIGS. 5-8 illustrate an electrode positioning element 3 according to the present invention, and FIGS. 9 and 10 illustrate an electrode adapted to fit the positioning element. The positioning element 3 comprises a substantially rectangular block 23, of plastic material for example, having a central opening 25 for the insertion of an electrode. A substantially star-shaped sleeve 27 is disposed within the opening 25 to provide electrical contact with the electrode. The sleeve 27, which should be made of a metal, such as silver, having a high electrical conductivity, is soldered to a wire 29 that extends outwardly in the block 23 through a radially extending opening 31 into a transverse opening 33. The wires 29 from other electrode positioning elements are collected and guided in the opening 33 as will be described below in connection with FIG. 11. The wire 29 is preferably low-noise cable, such as Microdot cable No. 250-3838, which minimizes the effect of movement artifacts on the transmitted signal.

The electrode intended for use with the electrode positioning element 3 illustrated in FIGS. 5-8 is shown in FIG. 9 (top view) and FIG. 10 (side view). This electrode 35 is made of a conductive sponge material of the type conventionally used in the electroencephalographic or electrocardiographic arts. The sponge is impregnated, at least partially, with a conductive cream or jell containing silver-silver chloride, for example, as an electrically conductive agent. Preferably, the electrode 35 has a recess 37 extending inward along its central axis from its lower end; i.e., the point which is to come in contact with the scalp. The recess 37 is filled with a conductive cream or jell, either during manufacture or subsequently, by the technician, when the encephalographic holder is placed on the head of a patient. After the electrode is inserted in position in the holder the cream or jell in the opening 37 is pressed into contact with the scalp and ensures that an adequate electrical connection is established therewith.

The electrode 35 is also made substantially star-shaped in cross-section so as to mate with the metal sleeve 27 when in position. The purpose of the star-shaped configuration is to prevent the possibility of rotation of the electrode 35 (as may occur upon movement of a patient's head if the electrode were cylindrical, for example) and to ensure that an adequate electrical connection will be made between the scalp and the metal sleeve 27. By bringing the metal sleeve closer to the center of electrode at the inside corners of the "star", the sleeve is brought closer to the point of contact with the scalp.

When the electrode 35 is inserted in the sleeve 27 in the opening of the electrode positioning element 3, it is retained against the scalp by means of flange portions 39 on the sides of the opening 25 at its outside edge, as viewed when the electrode positioning element 3 is in place on a head.

As is most clearly seen in FIGS. 6 and 7, the expandable and elastic elongate members or straps are connected to the block 23 with the aid of pins 41. The straps are folded over the pins and inserted sideways, together therewith, into a slot 43 along one side of the block 23. The slot 43 is configured with a narrow neck or opening along the side of the block so that, whereas the strap can extend through this neck, the pin cannot.

It will be appreciated that any other simple mechanism for attaching the elongate members to the block 23 may be substituted for the arrangement shown in FIGS. 6 and 7. For example, the blocks 23 may be molded onto the ends of the elongate members. In fact, the blocks 23 may be made of the same material as the elongate members so that the entire holder may be molded as a single monolithic element. Alternatively, the elongate members may be attached to the blocks 23 in the same manner in which a watchband is connected to a watch.

FIGS. 11 and 12 depict the electrical system of the holder according to a preferred embodiment of the present invention. FIG. 11 shows how each of the metal sleeves 27 in the blocks 23 is connected by means of a wire 29 to a terminal at the member 21. The wires 29 are guided along the paths of the elongate members 5, 7, 9 and 11 (which are not shown in FIG. 11 but are represented, in part, by the dotted dashed lines) and are held in position by the respective blocks 23 along the paths. As shown, the wires 29 are passed through the opening 33 in each successive block along their path.

FIG. 12 illustrates how the wires 29 may be connected to the electronic circuitry of the electroencephalographic instrument. In this preferred embodiment, the wires 29 terminate at a male electrical connector 45 having at least one connector element 47 associated with each wire. The electrical connector 45 is designed to mate with a suitable female connector 49 which may be detached when the electroencephalographic electrode holder according to the present invention is not in actual use on a patient's head.

The female connector 49 may be connected directly to the electronic circuitry of the electroencephalographic instrument by means of a cable 51, or may form a part of a preamplifier unit 53 in which is located a small preamplifier for each of the wires 29 and their associated electrodes. Power may be supplied to the preamplifier unit 53 from the cable 51 which, as mentioned above, is connected to the electronic circuitry of the electroencephalographic instrument. This power is thus supplied via additional terminals 55 and 57 arranged in line with the output terminals of the preamplifier 53.

It will be appreciated that additional control functions may be included in the preamplifier unit 53 in cases where it is desirable to place such functions as close as possible to the signal receiving electrodes. For example, the unit 53 may be provided with a plurality of lights (e.g., light emitting diodes), one for each wire 29, which indicate to the technician when proper electrical contact has been made between each electrode and the scalp.

It will be understood that the present invention is susceptible to various modifications, changes and adaptations which fall within its spirit and scope. Accordingly, it is intended that the present invention be limited only by the following claims and their equivalents.

I claim:

1. A self-adjustable holder for automatically positioning electroencephalographic electrodes on the head of an animal in accordance with the International 10/20 System, said holder comprising, in combination:
    a. cap means for positioning on the head of an animal, said cap means being expandable and elastic so as to self-adjust to a snug fit when in place on the head, said cap means comprising a plurality of elongate members as follows:
        1. a first member of generally circular shape of a size to surround the head in a substantially horizontal plane when said cap means is in place thereon;
        2. a second member of generally semi-circular shape attached to said first member at first and second points on opposite sides thereof, said second member being of a size to extend over the top of the head in a substantially vertical plane when said cap means is in place thereon;
        3. a third member of generally semi-circular shape attached to said first member at third and fourth points thereon, said third member being of a size to extend over the head substantially in a plane forming an angle with respect to said vertical plane of said second member; and
        4. a fourth member of generally semi-circular shape attached to said first member at fifth and sixth points thereon, said fourth member being of a size to extend over the head substantially in a plane forming an angle with respect to said vertical plane of said second member,
        said third and said fourth member being on opposite sides of said vertical plane; and
    b. a plurality of electrode positioning means attached to said cap means for holding associated electrodes in contact with the head when said cap means is in place thereon, said electrode positioning means being located on said cap means relative to each other so as to hold said associated electrodes at precise positions in accordance with the International 10/20 System.

2. The self-adjustable holder defined in claim 1, wherein said cap means is made of a stretchable material.

3. The self-adjustable holder defined in claim 2, wherein said material includes rubber.

4. The self-adjustable holder defined in claim 2, wherein said material includes a synthetic fiber mesh.

5. The self-adjustable holder defined in claim 1, wherein said cap means has a substantially hemispherical shape.

6. The self-adjustable holder defined in claim 1, wherein said first, second, third and fourth members are strap-shaped members.

7. The self-adjustable holder defined in claim 1, wherein said first, third and fifth points are substantially the same and are adapted to be positioned on the head at a precise location in relation to the nasion when said cap means is in place thereon, and wherein said second, fourth and sixth points are substantially the same and are adapted to be positioned on the head at a precise location in relation to the inion when said cap means is in place thereon.

8. The self-adjustable holder defined in claim 7, wherein said third and fourth members are each adapted to extend over the head substantially in a plane forming an angle of 45° with respect to said vertical plane of said second member.

9. The self-adjustable holder defined in claim 1, wherein said first and second points are adjacent the ears of the head when said cap means is in place thereon; wherein said third and fourth points are located, respectively, between said first and second points and the front of the head when said cap means is in place thereon; and wherein said fifth and sixth points are located, respectively, between said first and second points and the back of the head when said cap means is in place thereon.

10. The self-adjustable holder defined in claim 1, wherein said cap means includes means for precisely orienting and locating said cap means with respect to said at least one reference point when said cap means is in place on the head.

11. The self-adjustable holder defined in claim 10, wherein said reference point is the nasion of the head.

12. The self-adjustable holder defined in claim 10, wherein said reference point is the inion of the head.

13. The self-adjustable holder defined in claim 10, wherein said locating means includes a rigid member on opposite sides of said cap means adapted to be positioned at the nasion and the inion, respectively, of the head when said cap means is in place.

14. The self-adjustable holder defined in claim 1, wherein each electrode positioning means includes an element made of rigid material attached to said cap means and having an opening therethrough for the insertion of an associated electrode, said element comprising:
1. means for retaining the electrode once it is inserted in said opening; and
2. means for electrically contacting said electrode when it is inserted in said opening, whereby an electrode may be inserted in each of said electrode positioning elements after said cap means has been placed on a head.

15. The self-adjustable holder defined in claim 14, wherein said retaining means includes a flange portion on the outside edge of said opening, as viewed when said electrode positioning element is in place on a head, for preventing free travel of an electrode in said opening.

16. The self-adjustable holder defined in claim 14, wherein said electrical contacting means includes a metal sleeve arranged inside of said opening.

17. The self-adjustable holder defined in claim 16, wherein said sleeve is substantially star-shaped and is thereby adapted to eceive a substantially star-shaped electrode.

18. The self-adjustable holder defined in claim 16, wherein the metal of said sleeve includes silver.

19. The self-adjustable holder defined in claim 1, further comprising:
1. electrical connector means, attached to said cap means, for providing a detachable electrical connection for a plurality of wires; and
2. at least one wire connecting each electrode positioning means with said electrical connector means.

20. The self-adjustable holder defined in claim 19, further comprising a plurality of amplifiers arranged in a common unit, said unit having means providing a mating electrical connection with said electrical connector means, whereby each amplifier is connected to one electrode positioning means for amplifying the signal received at the electrode associated therewith.

* * * * *